(12) United States Patent
Riskin et al.

(10) Patent No.: US 9,610,559 B2
(45) Date of Patent: Apr. 4, 2017

(54) METHOD AND GENERATOR FOR GENERATION OF HYDROGEN PEROXIDE

(71) Applicants: Yefim Riskin, Katzrin (IL); Leonid Riskin, Maalot (IL)

(72) Inventors: Yefim Riskin, Katzrin (IL); Leonid Riskin, Maalot (IL)

(73) Assignee: OXYPRO, LTD, Katzrin (IL)

( * ) Notice: Subject to any disclaimer, the term of this patent is extended or adjusted under 35 U.S.C. 154(b) by 109 days.

(21) Appl. No.: 14/581,294

(22) Filed: Dec. 23, 2014

(65) Prior Publication Data

US 2016/0175803 A1    Jun. 23, 2016

(51) Int. Cl.

| | | |
|---|---|---|
| *B01J 19/08* | (2006.01) | |
| *A61L 9/03* | (2006.01) | |
| *A61L 9/22* | (2006.01) | |
| *C01B 15/027* | (2006.01) | |
| *H01T 19/00* | (2006.01) | |

(52) U.S. Cl.
CPC ........... *B01J 19/088* (2013.01); *A61L 9/03* (2013.01); *A61L 9/22* (2013.01); *C01B 15/027* (2013.01); *H01T 19/00* (2013.01); *A61L 2209/211* (2013.01); *B01J 2219/083* (2013.01); *B01J 2219/0809* (2013.01); *B01J 2219/0818* (2013.01); *B01J 2219/0849* (2013.01); *B01J 2219/0875* (2013.01); *B01J 2219/0884* (2013.01); *B01J 2219/0898* (2013.01)

(58) Field of Classification Search
None
See application file for complete search history.

(56) References Cited

U.S. PATENT DOCUMENTS

| | | |
|---|---|---|
| 3,440,800 A | 4/1969 | Messen-Jaschin |
| 5,380,355 A | 1/1995 | Brothers |
| 2016/0256847 A9* | 9/2016 | Mandle ............... C10G 29/205 |

FOREIGN PATENT DOCUMENTS

| | | |
|---|---|---|
| DE | 102009017807 | 11/2009 |
| EP | 2404621 | 1/2012 |
| WO | 9632175 | 10/1996 |
| WO | 2007130852 | 11/2007 |

OTHER PUBLICATIONS

International Search Report for PCT/IL2015/050897 dated Dec. 23, 2015 (5 pages).
International Written Opinion for PCT/IL2015/050897 dated Dec. 23, 2015 (5 pages).

* cited by examiner

*Primary Examiner* — Krishor Mayekar
(74) *Attorney, Agent, or Firm* — Niels Haun; Dann, Dorfman, Herrell and Skillman, P.C.

(57) ABSTRACT

A method and generator for generation of hydrogen peroxide which operate on the principle of conveying air-liquid or vapor flow through a corona discharge zone in air. Such devices can be used for disinfection of air and of various objects for industrial and home uses.

7 Claims, 1 Drawing Sheet

METHOD AND GENERATOR FOR GENERATION OF HYDROGEN PEROXIDE

FIELD OF THE INVENTION

Figure 1:
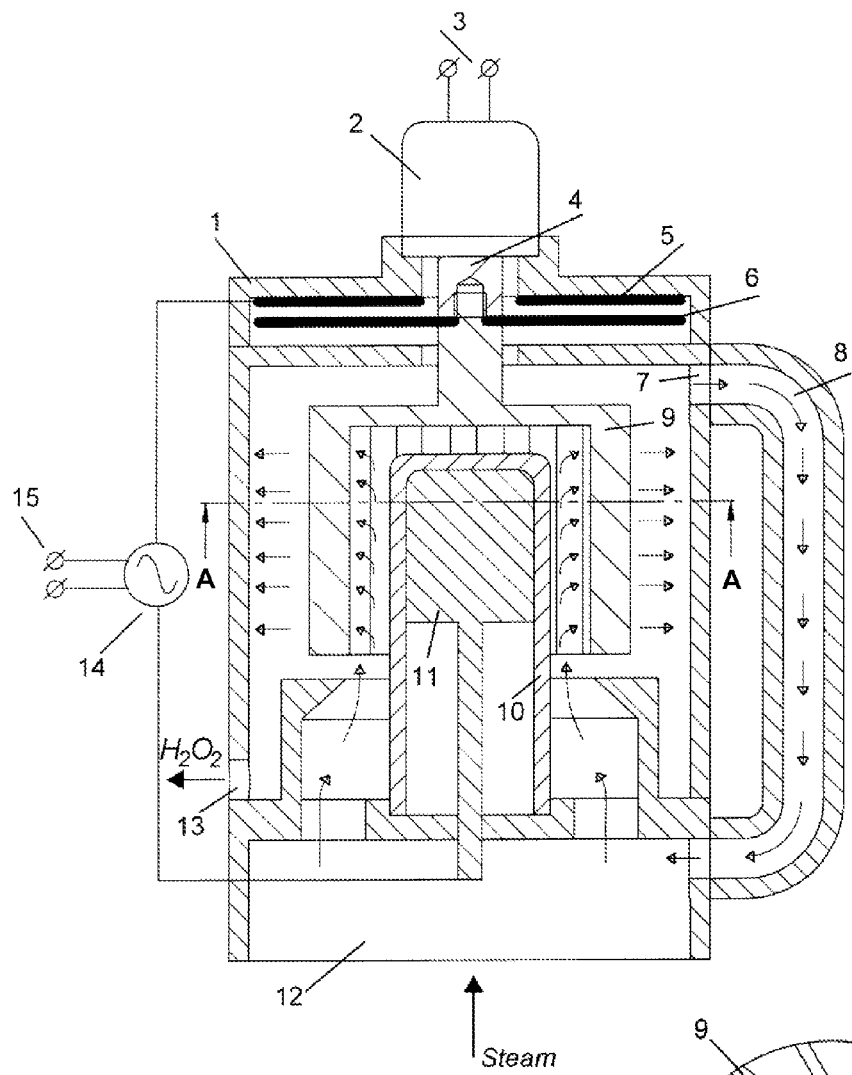

This invention relates to methods and devices for the generation of hydrogen peroxide operating on the principle of conveying air-liquid or vapor flow through a corona discharge zone in air.

BACKGROUND OF THE INVENTION

CN 1011569515 discloses a non-equilibrated plasma type spray sterilization disinfectant generating device, consisting of a main unit and a plasma spray head. A high voltage potential difference between metal electrodes in the plasma spray head is utilized to form a corona discharge where the distance between the metal electrodes is minimal. The corona discharge is driven by an air-water mixture generated by an atomization nozzle, so as to quickly slide downstream along an electrode surface and form a pulse type sliding arc discharging non-equilibrated plasma on the electrode surface. An air-water mixture containing hydrogen peroxide, ozone, oxyhydrogen free radical, oxygen free radical, and other oxidizable particles is produced and sprayed from the insulator casing to form air-water spray sterilization disinfectant.

It is also known to produce the air-liquid spray using an air compressor which conveys air at a high speed (50-100 m/sec) through a corona discharge zone.

The flow conveyed through the corona discharge zone contains hydrogen peroxide ($H_2O_2$) and ozone ($O_3$) which are delivered to the object being disinfected. A drawback of such a method is that part of the ozone is dissolved in the liquid, while the remainder is present in the airflow.

Also known is an approach in which the air-liquid spray is again produced by means of an air compressor and conveyed through a corona discharge zone, but is thereafter separated into liquid hydrogen peroxide and air which contains undissolved ozone in the liquid.

In order to remove the ozone, the air may be conveyed through an activated carbon filter.

A common disadvantage of the previous state of the art is its limited field of application which stems from the need for an air compressor.

SUMMARY OF THE INVENTION

An object of the present invention is therefore to provide a method and device for generating hydrogen peroxide which address disadvantages of the prior art.

This object is in the first place achieved by generating cold vapor, which is used as an air-liquid flow, using the well-known method of ultrasonic generation in water, thus avoiding use of the costly compressor.

Unlike the air-liquid flow generation by means of an air compressor which is related to jet technologies, cold vapor generation can be related to "cloud technologies", since the cloud vapor is generated under normal pressure when the vapor "cloud" remains immobile unless an external source is used to generate a pressure fall. A fan is generally used as such a source.

The proposed method is based on the use of a hollow rotor which performs three functions simultaneously.

1. Operates or drives one of the electrodes used to generate a corona discharge zone;
2. Generates a discharge zone for the cold vapor transfer into the corona discharge zone;
3. Operates as a liquid and air separator which uses centrifugal force produced by the rotor rotation.

The rotor or at least a part of it is made of a conducting material.

The other electrode which is coated with insulation is mounded inside the rotor cavity.

Power from a high voltage AC source is applied to the rotor from one of the terminals via capacitive coupling while the second terminal is directly connected to the second electrode. In this way a straight segment of corona discharge is generated between the rotor and the second electrode insulator.

The distance between the inner diameter of the rotor and the outer diameter of the second electrode insulator is determined from a consideration of the required corona discharge current produced at a preset magnitude of the high AC voltage.

The rotor shaped as a centrifugal fan rotor is rotated around the second electrode. The corona discharge zone is rotated too.

As mentioned before the cold vapor is drawn into and rotates within the corona discharge zone.

The rotational velocity of the rotor and the corona discharge zone is much higher than that of the cold vapor because of the strong impact of the corona discharge on the vapor. It is subjected to a strong influence of the corona discharge.

Vapor separation to liquid and air using centrifugal force produced by the rotor is attained by changing by 90° the direction of the cold vapor transmission through the straight segment of corona discharge between the electrodes. The above angle may change slightly depending on the electrodes configuration.

One of the advantages of the proposed method of $H_2O_2$ generation is the increase of the $H_2O_2$ concentration when hydrogen peroxide produced at the generator outlet in a liquid form is used to generate the vapor entering the generator. To do this the generator outlet is connected to a reservoir of liquid that is intended to be converted into vapor.

Actually the concentration is increased due to the proportional increase of the generator operation time.

A device according to the invention for generating hydrogen peroxide ($H_2O_2$) comprises:

A cylindrical body with a cold vapor inlet and an air and $H_2O_2$ outlets from the body, a bypass air channel, stator and rotor plates of air capacitor, a motor with a rotor plate of the air capacitor fastened to its axis and a rotor which together with the motor and the body form a centrifugal fan, an insulator with an electrode mounted inside the rotor cavity and a high AC voltage supply.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 is a schematic representation of a device for generating hydrogen peroxide according to the invention; and FIG. 2 is a partial cross-section through line A-A in FIG. 1.

DETAILED DESCRIPTION OF EMBODIMENTS

Referring to FIG. 1 there is shown a device for generating hydrogen peroxide comprising a housing 1 toward an upper end of which there are mounted an electric motor 2 having power supply terminals 3 and an axis 4. An air capacitor is formed of an annular stator plate 5 which is supported toward the upper end of the housing and a rotor plate 6, (constituting a first electrode) which together with a hollow rotor 9 are attached to the motor axis 4. Also provided toward the upper end of the housing is an air outlet 7. An insulator 10 containing therein an electrode 11 constituting a second electrode is fixedly mounted inside the hollow rotor 9. A cold vapor inlet 12 and an H2O2 outlet 13 are formed in a lower part of the housing 1. The air outlet 7 is connected to the cold vapor inlet 12 via a bypass channel 8. A high voltage AC supply 14 fed by input terminals 15 has outputs connected to the stator plate 5 of the air capacitor (whereby it is capacitively coupled to the first electrode constituted by the rotor plate 6) and to the second electrode 11.

The device operates as follows. As power is applied to the terminals 3 of the motor 2, the motor axis 4 rotates together with the rotor plate 6 of the air capacitor and the rotor 9, both of which are fastened to the motor axis 4. As power is applied to the terminals 15 of the high AC voltage supply 14, the stator plate 5 of the air capacitor and 25 the second electrode 11 are energized. In this way the high voltage AC is applied via the air capacitor to the rotor 9 and the second electrode 11 enclosed within the insulator 10.

Figure 2:
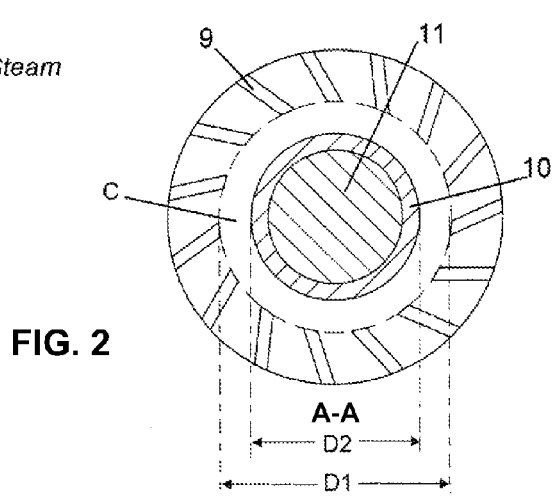

A barrier corona discharge zone shown as C in FIG. 2 is generated between the insulator 10 and the rotor 9 and is rotated together with the rotor 9 relative to the fixed insulator 10. At the same time, a low pressure zone created between the rotor 9 and the 30 insulator 10 sucks in the cold vapor from the vapor inlet 12 into the corona discharge zone C. The vapor that passes through the corona discharge zone turns to hydrogen peroxide ($H_2O_2$) and changes its initial flow direction in the zone by 90°.

Also referring to FIG. 2 it is seen that the corona discharge zone C is formed within the annular space between the inner diameter D1 of the rotor 9 and the outer diameter D2 of the insulator 10 surrounding the second electrode 11. The distance between D1 and D2 is determined from a consideration of the required corona discharge current produced at a preset magnitude of the high AC voltage.

Since centrifugal force is generated during rotation of the rotor 9, large groups of liquid molecules composing the vapor are repelled to the cylindrical inner walls of the housing 1 forming drops of $H_2O_2$ which flow down along the inner walls and are removed from the device via the $H_2O_2$ outlet 13 in the lower part of the housing 1.

As a result of the liquid separation process described above, air containing a certain amount of vaporous $H_2O_2$ and ozone $O_3$ undissolved in the liquid remains in the device. Escape of air containing the above components from the device is undesirable. Therefore the air exiting the air outlet 7 is conveyed via the by-pass channel 8 to the cold vapor inlet 12 which allows for vapor injection into the device 10.

By such means, recycled air circulates within in a closed space inside the device, thus obviating the need for an activated carbon filter and simplifying the design and maintenance of the device.

A prototype of the device constructed using the proposed method has the following specification:

| | |
|---|---|
| Insulator material | Glass |
| Distance between the insulator of the first electrode and the second electrode | 1 mm |
| The rotor rotation velocity | 6000 RPM |
| The AC voltage source amplitude | ±7 kV |
| The AC voltage source frequency | 40 kHz |
| Vapor consumption | 300 mL/h |
| $H_2O_2$ concentration at the generator outlet | 100 ppm |

The invention claimed is:

1. Device for generating hydrogen peroxide, the device comprising:
   a housing having inner walls containing an inlet for an air-liquid or a vapor and separate outlets for $H_2O_2$ and air outflow,
   first and second electrodes positioned within the housing so as to create a space within which the air-liquid or the vapor is able to flow, and
   a high AC voltage supply connected to the first and second electrode configured to generate between the electrodes a corona discharge having a straight segment; wherein:
   a hollow centrifugal fan rotor is mounted inside the housing and is operatively coupled to a motor for rotating about an axis;
   an open end of the hollow rotor faces the inlet so that incoming air-liquid or vapor flows into the hollow rotor;
   a corona discharge zone is formed between an inner wall of the rotor and an outer wall of the second electrode which is at least partially disposed within a cavity of the rotor;
   the air-liquid or vapor passing through the corona discharge zone is repelled radially by the rotor to the inner walls of the housing; and
   the rotor changes a direction of the air-liquid or vapor flow within the straight segment of the corona discharge.

2. The device according to claim 1, wherein at least part of the rotor is made from an electrically conducting material.

3. The device according to claim 1, wherein the high AC voltage supply is connected to the rotor via a capacitive coupling.

4. The device according to claim 1, wherein the second electrode is surrounded by an insulator and is disposed within a cavity of the centrifugal fan rotor.

5. The device according to claim 4, wherein an inner diameter of the rotor is displaced from an outer diameter of the insulator by a predetermined gap, a length of which is selected so as to derive a required corona discharge current at a preset magnitude of the high AC voltage supply.

6. The device according to claim 1, wherein the air outlet and the inlet are connected by a bypass channel.

7. The device according to claim 1, wherein the first electrode is an annular electrode rotatably attached to the rotor and is capacitively coupled to the high AC voltage supply via a static electrode fixed to the housing.

* * * * *